(12) United States Patent
Tojo et al.

(10) Patent No.: US 12,245,832 B2
(45) Date of Patent: Mar. 11, 2025

(54) SURGICAL ASSIST ROBOT AND METHOD OF CONTROLLING THE SAME

(71) Applicants: KAWASAKI JUKOGYO KABUSHIKI KAISHA, Kobe (JP); MEDICAROID CORPORATION, Kobe (JP)

(72) Inventors: Tsuyoshi Tojo, Kobe (JP); Nobuyasu Shimomura, Kobe (JP); Tetsuo Ichii, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 0 days.

(21) Appl. No.: 17/782,216

(22) PCT Filed: Dec. 4, 2020

(86) PCT No.: PCT/JP2020/045270
§ 371 (c)(1),
(2) Date: Jun. 3, 2022

(87) PCT Pub. No.: WO2021/112229
PCT Pub. Date: Jun. 10, 2021

(65) Prior Publication Data
US 2023/0014033 A1   Jan. 19, 2023

(30) Foreign Application Priority Data
Dec. 5, 2019 (JP) .................................. 2019-220758

(51) Int. Cl.
*A61B 34/37* (2016.01)
*A61B 17/34* (2006.01)
(Continued)

(52) U.S. Cl.
CPC .............. *A61B 34/37* (2016.02); *A61B 17/34* (2013.01); *A61B 34/75* (2016.02); *A61B 2034/302* (2016.02)

(58) Field of Classification Search
CPC ......... A61B 34/37; A61B 34/75; A61B 17/34; A61B 2034/302
See application file for complete search history.

(56) References Cited

U.S. PATENT DOCUMENTS

2012/0132018 A1* 5/2012 Tang ...................... A61B 34/70
74/25
2014/0148817 A1   5/2014 Hasegawa et al.
(Continued)

FOREIGN PATENT DOCUMENTS

JP   2013-034862 A   2/2013
JP   2016-516487 A   6/2016

*Primary Examiner* — Jason Holloway
*Assistant Examiner* — Christopher A Buksa
(74) *Attorney, Agent, or Firm* — METROLEX IP LAW GROUP, PLLC; Robert L. Scott, Esq.

(57) ABSTRACT

A surgical robot includes: a surgical instrument; a manipulator that supports a surgical instrument without holding a trocar and includes an instrument interface to which the surgical instrument is attached, an arm including rotational joints, and a prismatic joint; and a controller. The controller may store a center of motion of the surgical instrument and control motion of the manipulator such that with the shaft inserted through the trocar and the tool located in a body cavity of the patient, a relationship $T1 \geq L$ is established in a case of $L \leq T0$, wherein: L represents an intra-body cavity length of the surgical instrument; T0 represents a maximum possible linear movement amount of the prismatic joint from an origin position along the axial direction; and T1 represents a first linear movement amount of the prismatic joint from the origin position to a current position along the axial direction.

18 Claims, 12 Drawing Sheets

(51) Int. Cl.
*A61B 34/00* (2016.01)
*A61B 34/30* (2016.01)

(56) References Cited

U.S. PATENT DOCUMENTS

2014/0276952 A1 9/2014 Hourtash et al.
2019/0159851 A1 5/2019 Karguth et al.
2020/0405403 A1* 12/2020 Shelton, IV ....... A61B 17/3421

* cited by examiner

SURGICAL ASSIST ROBOT AND METHOD OF CONTROLLING THE SAME

CROSS-REFERENCE TO RELATED APPLICATIONS

This application is a national stage entry of International Application No. PCT/JP2020/045270 filed on Dec. 4, 2020, which claims priority based on the Article 8 of Patent Cooperation Treaty from the prior Japanese Patent Application No 2019-220758, filed on Dec. 5, 2019, the entire contents of all of which are incorporated herein by reference.

TECHNICAL FIELD

The present invention relates to surgical robots.

BACKGROUND ART

Robotic surgical systems for minimally invasive surgery have been conventionally known. Such a robotic surgical system typically includes: a surgical robot (slave device) including a surgical instrument and a manipulator supporting the surgical instrument; a master device directly operated by a surgeon; and a controller that controls the surgical instrument and the manipulator such that the surgical instrument moves in response to operations received by the master device. Patent Literature 1 discloses this kind of robotic surgical system.

The robotic surgical system of Patent Literature 1 includes a surgeon console and a patient-side cart (an example of surgical robots) remotely operated by the surgeon console. The patient-side cart includes manipulator arms and a surgical instrument replaceably coupled to an instrument holder disposed at the distal end of each manipulator arm. The surgical instrument includes a base coupled to the instrument holder, an elongate shaft connected to the base, and a tool coupled to the distal end of the shaft. A cannula (or a sleeve of a trocar) is retained at a minimally invasive incision of a body wall of a patient, the shaft is passed through the cannula, and the tool is inserted into a body cavity of the patient through the cannula.

Patent Literature 1 teaches that the movement of the surgical instrument is constrained during robotic surgery to allow the shaft of the surgical instrument to pivot about a remote center. The remote center is defined at or near the minimally invasive incision (or the cannula retained at the incision) so as to minimize the size of the minimally invasive incision. In the robotic surgical system of Patent Literature 1, the cannula and the surgical instrument are supported by the instrument holder of one manipulator arm such that the minimally invasive incision and the remote center can be positioned relative to each other using the cannula. The surgical instrument can be inserted into or removed out of the body cavity of the patient through the remote center by sliding the surgical instrument linearly along the instrument holder.

CITATION LIST

Patent Literature

PTL 1: Japanese Laid-Open Patent Application Publication (Translation of PCT Application) No. 2016-516487

SUMMARY OF INVENTION

Technical Problem

In the surgical robot of Patent Literature 1, three or four tubes such as cannulas or trocar sleeves are placed in the patient. Instrument holders are disposed to hold the tubes, respectively. The instrument holders crowd around the surgical site and obstruct the work of assistants during surgery. In the event of an emergency situation during surgery using the surgical robot as described above, a possible way of addressing the situation is to withdraw the tool of the surgical instrument inserted in the body cavity to a location where the tool does not contact the patient's tissue. This withdrawal should be performed quickly and reliably.

It is therefore an object of the present invention to provide: a surgical robot capable of ensuring a larger workspace around a surgical site and more quickly withdrawing a tool of a surgical instrument from a body cavity than conventional surgical robots; and a method of controlling the surgical robot.

Solution to Problem

One of candidate locations to which the tool of the surgical instrument is withdrawn is the interior of a trocar retained at the body wall of the patient. The interior of the trocar can be the withdrawal location closest to the tool located in the body cavity of the patient. Placing the tool in the interior of the trocar prevents contact between the patient's tissue and the tool.

In the surgical robot as described above, the manipulators have redundant degrees of freedom so as to avoid interfering with one another. Thus, the manipulator holding the surgical instrument can move not one but two or more joints when the surgical instrument is inserted into or removed out of the body cavity of the patient. However, when the tool of the surgical instrument is withdrawn from the body cavity, it is desirable for the manipulator to move only one prismatic joint in order to reduce shaking of the shaft passing through the trocar and increase the passing speed of the shaft.

In view of the above circumstances, a surgical robot according to one aspect of the present invention includes:

a surgical instrument including a base disposed at a proximal end of the surgical instrument, a tool disposed at a distal end of the surgical instrument, and a shaft extending in an axial direction between the base and the tool;

a manipulator that supports the surgical instrument without holding a trocar retained at a body wall of a patient, the manipulator including an instrument interface to which the base is attached, an arm including rotational joints, and a prismatic joint coupling the instrument interface to a distal end of the arm; and a controller configured to store a remote center that is a center of motion of the surgical instrument, and control motion of the manipulator such that with the shaft inserted through the trocar and the tool located in a body cavity of the patient, a relationship $T1 \geq L$ is established in case of $L \leq T0$, wherein: L represents an intra-body cavity length of the surgical instrument, the intra-body cavity length being a length from the remote center to the distal end of the surgical instrument; T0 represents a maximum possible linear movement amount of the prismatic joint, the maximum possible linear movement amount being a maximum possible amount of linear movement from an origin position along the axial direction; and T1 represents a first linear movement amount of the prismatic joint, the first linear movement amount being an amount of linear movement from the origin position to a current position along the axial direction.

A surgical robot control method according to one aspect of the present invention is a method of controlling a surgical robot, the surgical robot including: a surgical instrument including a base disposed at a proximal end of the surgical instrument, a tool disposed at a distal end of the surgical instrument, and a shaft extending in an axial direction between the base and the tool; and a manipulator that supports the surgical instrument without holding a trocar retained at a body wall of a patient, the manipulator including an instrument interface to which the base is attached, an arm including rotational joints, and a prismatic joint coupling the instrument interface to a distal end of the arm, the method including:

storing a remote center that is a center of motion of the surgical instrument; and controlling motion of the manipulator such that with the shaft inserted through the trocar and the tool located in a body cavity of the patient, a relationship $T1 \geq L$ is established in case of $L \leq T0$, wherein: L represents an intra-body cavity length of the surgical instrument, the intra-body cavity length being a length from the remote center to the distal end of the surgical instrument; T0 represents a maximum possible linear movement amount of the prismatic joint, the maximum possible linear movement amount being a maximum possible amount of linear movement from an origin position along the axial direction; and T1 represents a first linear movement amount of the prismatic joint, the first linear movement amount being an amount of linear movement from the origin position to a current position along the axial direction.

In the above surgical robot and control method thereof, the tool of the surgical instrument can be withdrawn from the body cavity of the patient only by the control (withdrawal control) for returning the prismatic joint of the manipulator to the origin position.

In the withdrawal control, the shaft of the surgical instrument can be moved only along the axial direction. Moving the shaft only along the axial direction reduces shaking of the shaft and makes galling less likely to occur between the trocar and the shaft. Since the shaft can be smoothly pulled out of the trocar, the load imposed on the body wall can be reduced.

In the surgical robot configured as described above and the control method thereof, the trocar is not held by any instrument holder supporting the surgical instrument, unlike in conventional surgical robots. This can reduce the crowding of instrument holders around the surgical site.

In the surgical robot configured as described above, the controller may be configured to control the motion of the manipulator such that a relationship $(T1+T2) \geq L$ is established in case of $L>T0$, wherein T2 represents a second linear movement amount of the distal end of the arm, the second linear movement amount being an amount of linear movement effected along the axial direction by motion of at least one of the rotational joints.

The control method of the surgical robot configured as described above may include controlling the motion of the manipulator such that a relationship $(T1+T2) \geq L$ is established in case of $L>T0$, wherein T2 represents a second linear movement amount of the distal end of the arm, the second linear movement amount being an amount of linear movement effected along the axial direction by motion of at least one of the rotational joints.

In the above surgical robot and control method thereof, the tool of the surgical instrument can be withdrawn from the body cavity of the patient only by the control (withdrawal control) for returning the prismatic joint of the manipulator to the origin position and rotating at least one of the rotational joints as necessary.

Advantageous Effects of Invention

The present invention enables a surgical robot to ensure a larger workspace around a surgical site and more quickly withdraw a tool of a surgical instrument from a body cavity than conventional surgical robots.

DESCRIPTION OF EMBODIMENTS

Figure 1:
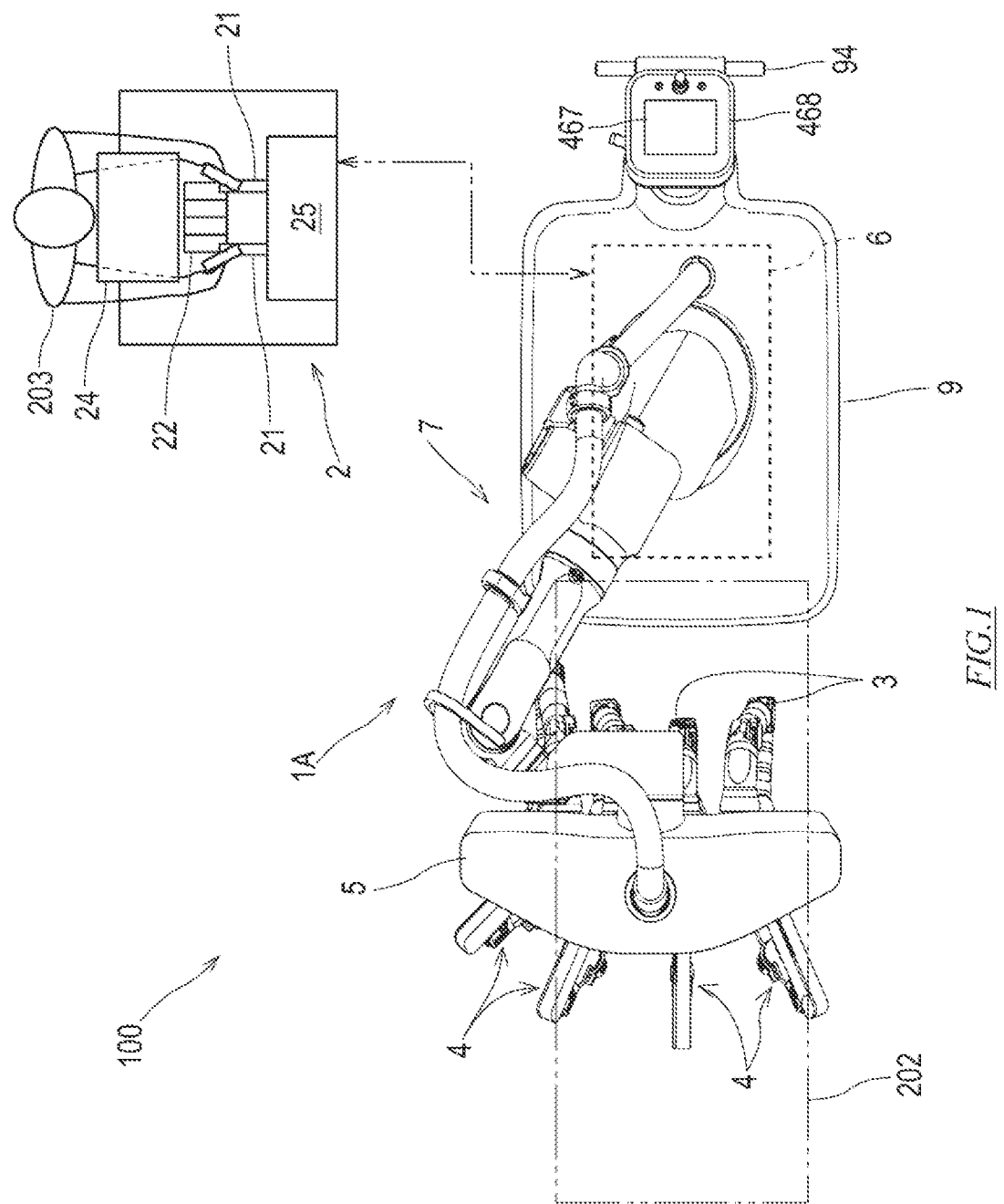
FIG. 1 is a plan view showing an overall configuration of a surgical system including a surgical robot according to one embodiment of the present invention.

FIG. 1 is a plan view showing an overall configuration of a surgical system 100 including a surgical robot 1A according to a first embodiment of the present invention. The surgical system 100 shown in FIG. 1 includes the surgical robot 1A as a patient-side system and a console 2 as a surgeon-side system.

[Console 2]

The console 2 is a device that receives operation inputs provided to the surgical system 100 from a surgeon 203. The console 2 is used to remotely operate the surgical robot 1A and placed inside or outside a surgery room. The console 2 includes operation input tools, a monitor 24, and a console controller 25. The operation input tools include at least one selected from a manually-operated manipulator arm 21, a foot-operated pedal 22, a touch panel display, a manually-operated button, and a manually-operated lever. The console controller 25 controls the monitor 24 to display an image captured by an endoscope 29 (see FIG. 8) which is one of surgical instruments 4. The surgeon 203 maneuvers the operation input tools while viewing an affected zone (surgical site) displayed on the monitor 24. The console controller 25 acquires operation inputs received by the operation input tools and transmits the operation inputs, by wire or wirelessly, to a robot controller 6 described later.

[Surgical Assist Robot 1A]

The surgical robot 1A is placed in the surgery room and near a surgical bed 202 on which a patient 201 lies. The interior of the surgery room is a sterile field subjected to sterilization.

Figure 2:
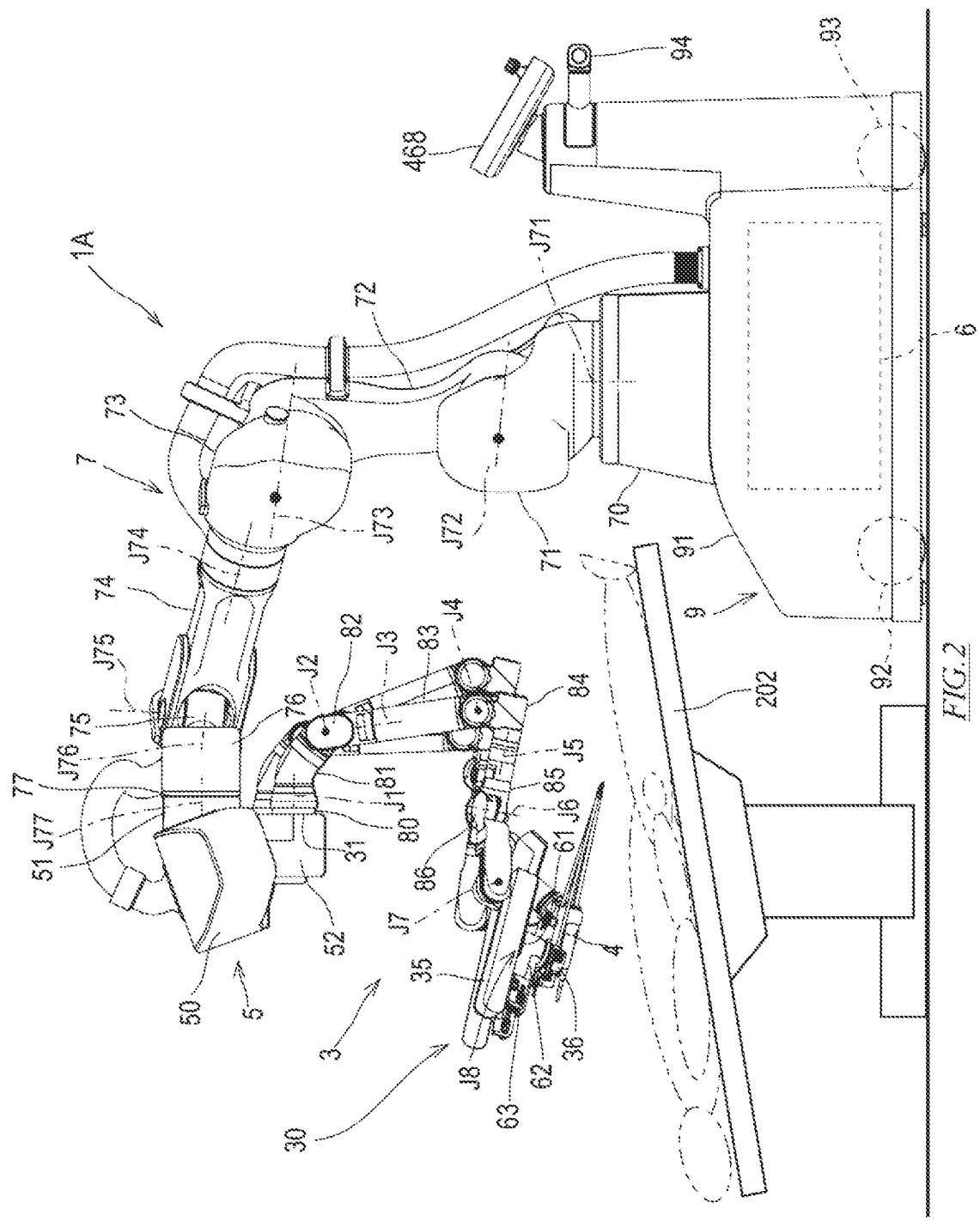
FIG. 2 is a side view of the surgical robot.

FIG. 2 is a side view of the surgical robot 1A. The surgical robot 1A shown in FIGS. 1 and 2 includes: a cart 9; a positioner 7 supported by the cart 9; a platform 5 coupled to the distal end of the positioner 7; patient-side manipulators (simply referred to as "manipulators 3" hereinafter) removably mounted on the platform 5; surgical instruments 4 attached to the respective distal ends of the manipulators 3; and a robot controller 6. These elements of the surgical robot 1A are serially connected in order from the cart 9 to the surgical instruments 4. For the serially connected elements, their ends directed towards the cart 9 are herein referred to as "proximal ends", and the opposite ends are herein referred to as "distal ends".

[Cart 9]

The cart 9 includes a cart body 91, front wheels 92, rear wheels 93, and a handle 94. The surgeon 203 or a surgery assistant can grip the handle 94 and steer the cart 9 to move the surgical robot 1A to any desired location. The cart 9 is fixed in position during surgery.

[Positioner 7]

The positioner 7 according to the present embodiment is configured as a seven-axis vertical articulated robot arm. The positioner 7 moves the platform 5 three-dimensionally relative to the cart 9. The positioner 7 is not limited to that in the present embodiment, and a vertical articulated robot arm having less or more than seven axes or a horizontal articulated robot arm may be used as the positioner 7.

The positioner 7 includes a base 70 mounted on the cart 9 and positioner links 71 to 76 connected in series. The positioner links 71 to 76 include: a first link 71 turnably coupled to the base 70 via a first joint J71; a second link 72 pivotally coupled to the first link 71 via a second joint J72; a third link 73 pivotally coupled to the second link 72 via a third joint J73; a fourth link 74 turnably coupled to the third link 73 via a fourth joint J74; a fifth link 75 pivotally coupled to the fourth link 74 via a fifth joint J75; a sixth link 76 turnably coupled to the fifth link 75 via a sixth joint J76; and a mechanical interface 77 turnably coupled to the sixth link 76 via a seventh joint J77. The platform 5 is coupled to the mechanical interface 77.

[Platform 5]

As shown in FIGS. 1 and 2, the platform 5 functions as a hub for the manipulators 3. In the present embodiment, the combination of the cart 9, positioner 7, and platform 5 constitutes a manipulator support movably supporting the manipulators 3.

The platform 5 includes a main body 50, a positioner coupler 51 disposed at the proximal end of the main body 50, and manipulator couplers 52 disposed at the distal end of the main body 50. The positioner coupler 51 is coupled to the mechanical interface 77 of the positioner 7. The main body 50 has a longitudinal direction and is arch-shaped with the cord extending in the longitudinal direction. The manipulator couplers 52 are arranged at discrete locations in the longitudinal direction of the main body 50. In the present embodiment, the number of the manipulator couplers 52 is four. The proximal end of each of the manipulators 3 is removably coupled to a corresponding one of the manipulator couplers 52.

[Patient-Side Manipulator 3]

Figure 3:
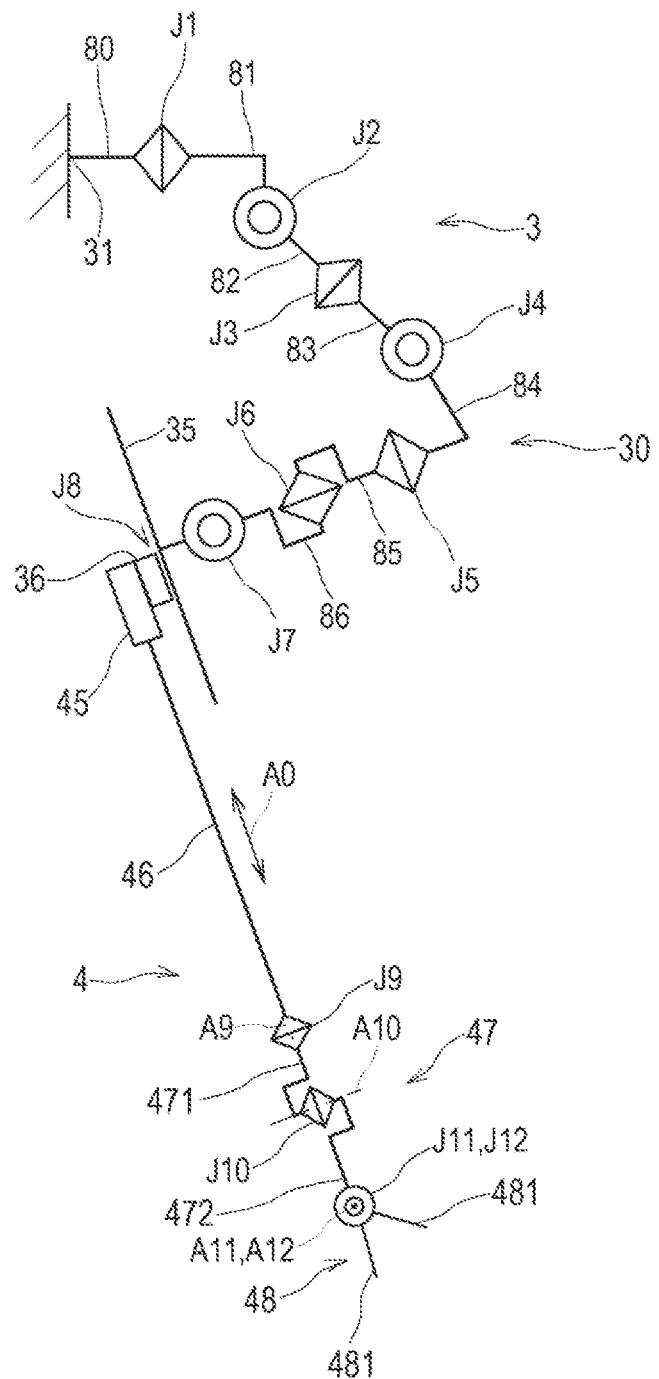
FIG. 3 shows axis configurations of a manipulator and a surgical instrument.

The manipulators 3 have substantially the same structure. FIG. 3 shows axis configurations of each manipulator 3 and surgical instrument 4. As shown in FIGS. 2 and 3, each manipulator 3 includes a first interface 31 disposed at the proximal end of the manipulator 3, a second interface 36 (instrument interface) disposed at the distal end of the manipulator 3, and an arm 30 connecting the first and second interfaces 31 and 36. The first interface 31 is coupled to the manipulator coupler 52 of the platform 5. A surgical instrument 4 including an endoscope 29 is coupled to the second interface 36 of one of the manipulators 3. A surgical instrument 4 for a surgical procedure is coupled to the second interface 36 of at least one of the manipulators 3.

The arm 30 includes a base 80 having the first interface 31 and arm links 81 to 86 connected in series. The arm links 81 to 86 include: a first link 81 turnably coupled to the base 80 via a first joint J1; a second link 82 pivotally coupled to the first link 81 via a second joint J2; a third link 83 turnably coupled to the second link 82 via a third joint J3; a fourth link 84 pivotally coupled to the third link 83 via a fourth joint J4; a fifth link 85 turnably coupled to the fourth link 84 via a fifth joint J5; and a sixth link 86 pivotally coupled to the fifth link 85 via a sixth joint J6. A linear-motion frame 35 is pivotally coupled to the sixth link 86 via a seventh joint J7.

The second interface 36 is coupled to the linear-motion frame 35 via an eighth joint J8. The eighth joint J8 is a prismatic joint coupling the second interface 36 to the linear-motion frame 35 such that the second interface 36 is linearly movable relative to the linear-motion frame 35. The eighth joint J8 includes a rail 61 disposed on the linear-motion frame 35 and a slider 62 slidable on the rail 61. The slider 62 is coupled to the second interface 36.

[Surgical Instrument 4]

The surgical instrument 4 includes a base 45 disposed at the proximal end of the surgical instrument 4, a tool 48 disposed at the distal end of the surgical instrument 4, and a shaft 46 connecting the base 45 and the tool 48. A wrist 47 is disposed between the shaft 46 and the tool 48.

The base 45 is removably attached to the second interface 36 of the manipulator 3. The shaft 46 is an elongate, hard tubular member and extends in an axial direction A0. With the surgical instrument 4 attached to the second interface 36 of the manipulator 3, the direction in which the rail 61 extends and the axial direction A0 of the surgical instrument 4 are parallel. Thus, sliding of the slider 62 on the rail 61 leads to the surgical instrument 4 moving in the axial direction A0 relative to the linear-motion frame 35.

The wrist 47 includes at least one wrist joint. The wrist 47 of the surgical instrument 4 illustrated in FIG. 3 includes a first wrist link 471, a second wrist link 472, a first wrist joint J9 connecting the shaft 46 and the first wrist link 471, a second wrist joint J10 connecting the first wrist link 471 and the second wrist link 472, and a third wrist joint J11 connecting the second wrist link 472 and the tool 48. The first wrist joint J9 permits the first wrist link 471 to rotate about a first axis A9 relative to the base 45. The first axis A9 coincides with the central axis of the shaft 46 and is parallel to the axial direction A0 of the surgical instrument 4. The second wrist joint J10 permits the second wrist link 472 to rotate about a second axis A10 relative to the first wrist link 471. The second axis A10 is substantially orthogonal to the first axis A9. The third wrist joint J11 permits the tool 48 to rotate about a third axis A11. The third axis A11 is substantially orthogonal to the first and second axes A9 and A10. The tool 48 according to the present embodiment is in the form of forceps and includes a pair of jaw members 481. The tool 48 includes a tool joint J12 that permits the pair of jaw members 481 to rotate about the third axis A11. The pair of jaw members 481 are rotated in opposite directions by the tool joint J12, and thus the jaw of the forceps is opened or closed.

[Variant of Surgical Robot 1A]

Figure 4:
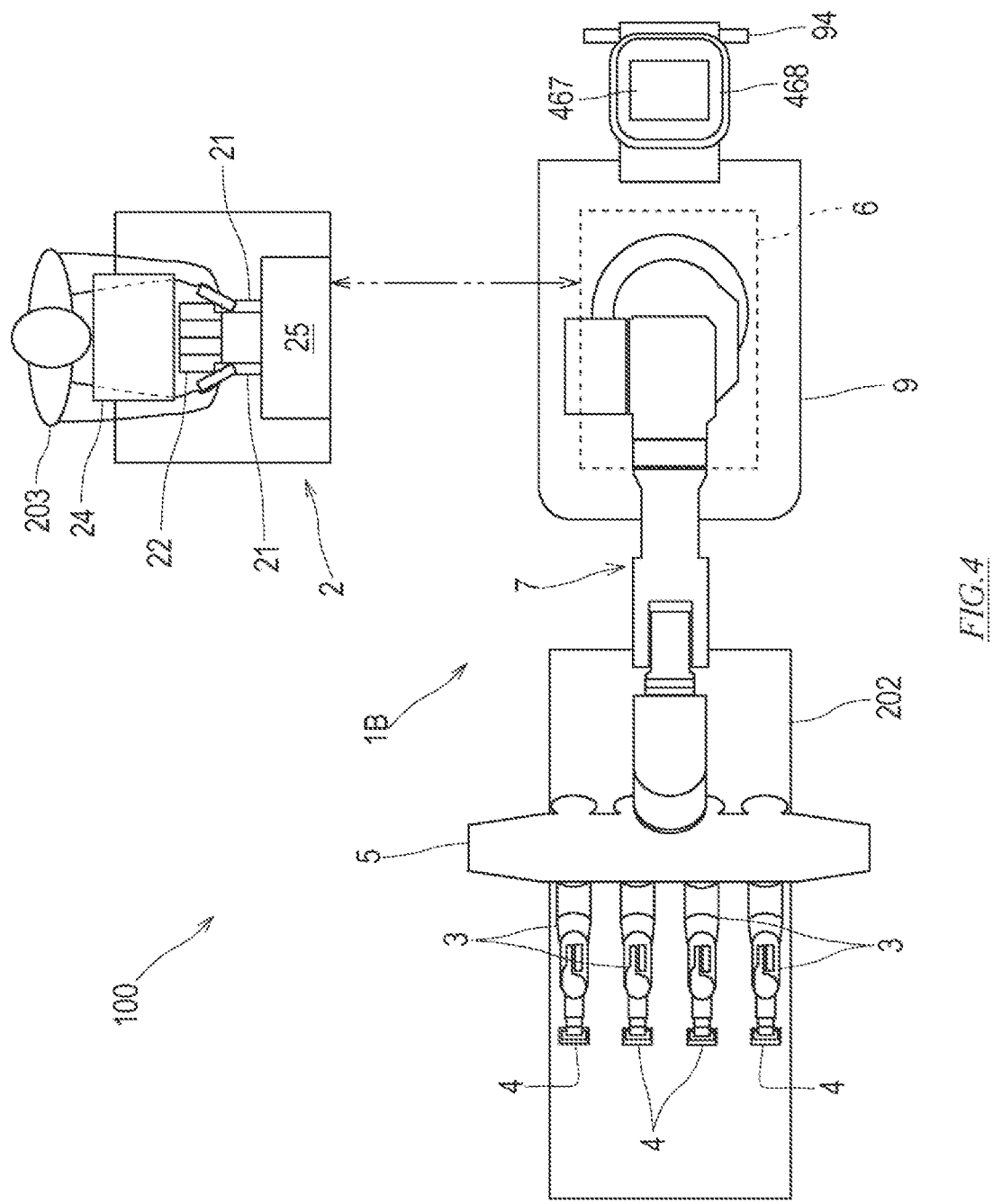
FIG. 4 is a plan view showing an overall configuration of a surgical system including a surgical robot according to a first variant.
Figure 5:
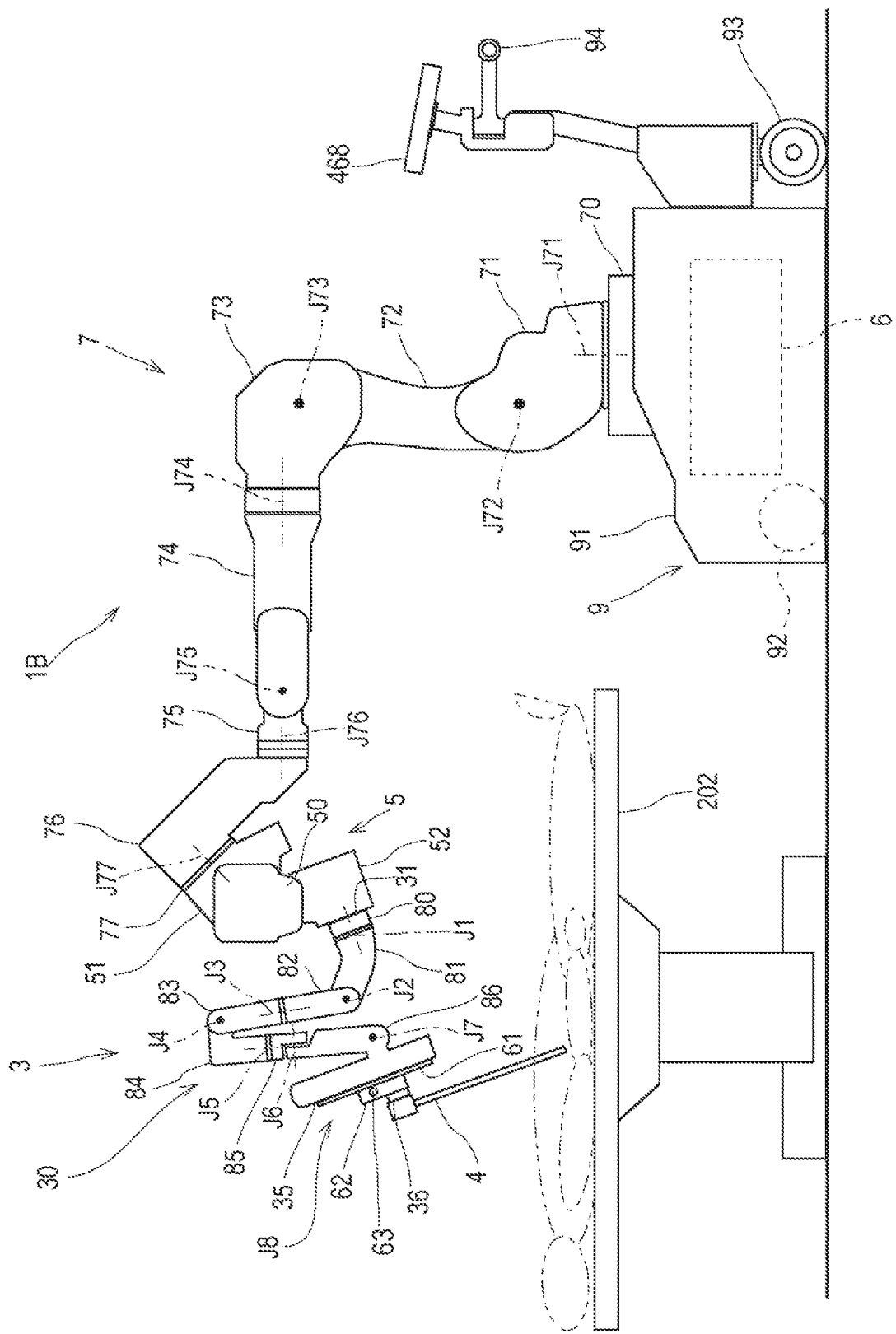
FIG. 5 is a side view of the surgical robot according to the first variant.
Figure 6:
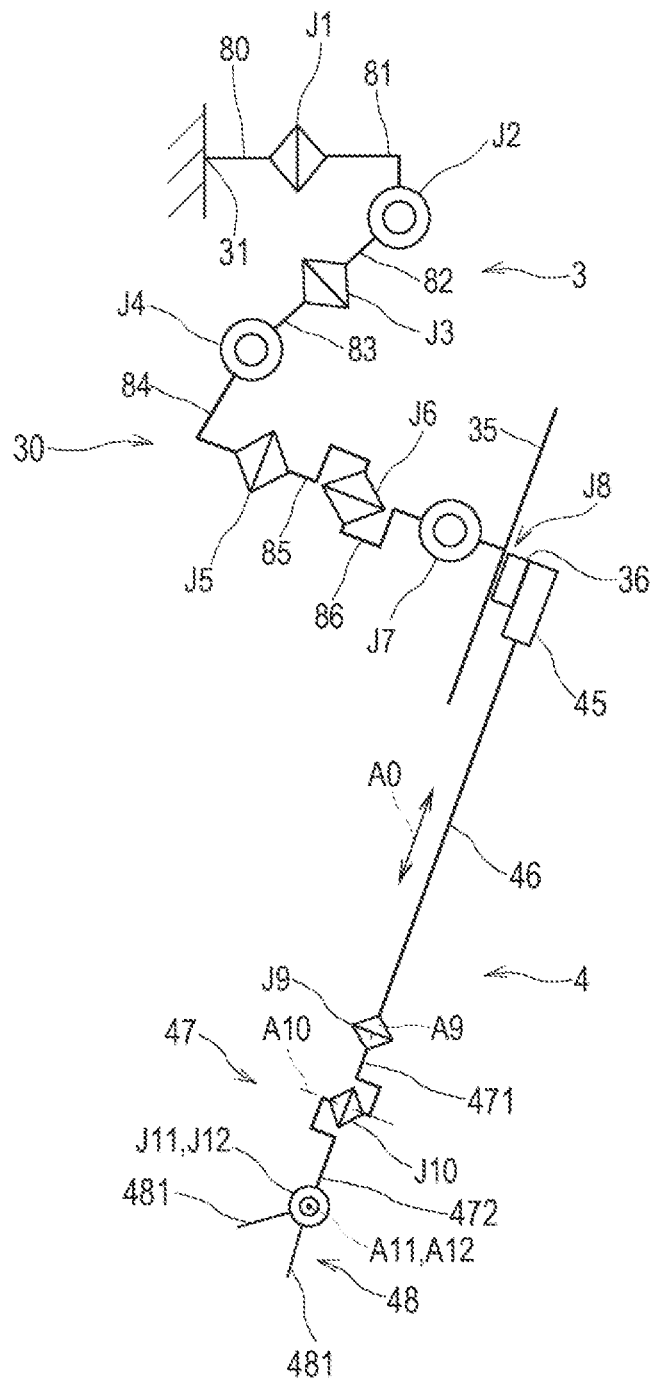
FIG. 6 shows axis configurations of a manipulator and a surgical instrument of the surgical robot according to the first variant.

FIG. 4 is a plan view showing an overall configuration of a surgical system 100 including a surgical robot 1B according to a first variant, FIG. 5 is a side view of the surgical robot 1B according to the first variant, and FIG. 6 shows axis configurations of each manipulator 3 and surgical instrument 4 of the surgical robot 1B according to the first variant. In the description of this variant, members which are the same as or similar to those of the above embodiment are denoted by the same reference signs in the drawings and will not be described again.

As shown in FIGS. 4 to 6, the surgical robot 1B according to the first variant, like the surgical robot 1A according to the above embodiment, includes: a cart 9; a positioner 7 supported by the cart 9; a platform 5 coupled to the distal end of the positioner 7; manipulators 3 removably mounted on the platform 5; surgical instruments 4 attached to the respective distal ends of the manipulators 3; and a robot controller 6. The surgical robot 1A according to the above embodiment and the surgical robot 1B according to the first variant differ in that the bases of the manipulators 3 are connected to the back surface of the platform 5 in the surgical robot 1A, while in the surgical robot 1B the bases of the manipulators 3 are connected to the front surface of the platform 5. The "back surface" of the platform 5 refers to that surface of the platform 5 which, as shown in FIGS. 1, 2, 4, and 5, faces towards the handle 94 of the cart 9 when the surgical robot 1A or 1B is in a basic posture, and the "front surface" of the platform 5 is the surface opposite to the back surface of the platform 5.

This means that the surgical robot 1A and the surgical robot 1B according to the first variant differ in the direction in which the first links 81 of the manipulators 3 extend relative to the platform 5. Thus, as shown in FIG. 6, the basic postures of the first link 81, second link 82, and second joint J2 connecting these links in the surgical robot 1B are different from those in the surgical robot 1A. Except for this difference, the axis configurations of each manipulator 3 and surgical instrument 4 of the surgical robot 1B according to the first variant are substantially the same as those of each manipulator 3 and surgical instrument 4 of the surgical robot 1A.

[Drive System Configurations of Surgical Robots 1A and 1B]

Figure 7:
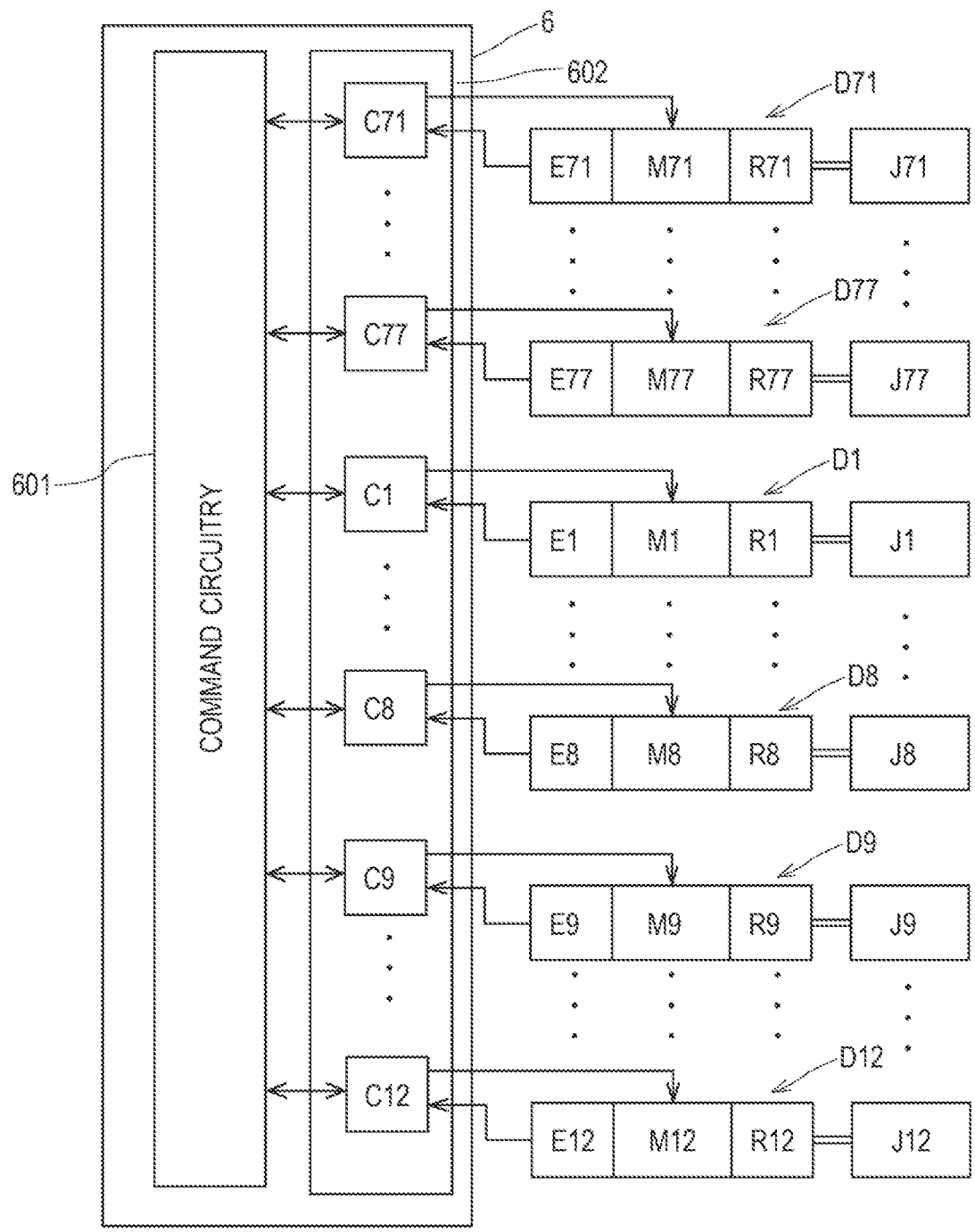
FIG. 7 shows a drive system configuration for a positioner, a manipulator, and a surgical instrument.

FIG. 7 shows a drive system configuration for the positioner 7, manipulator 3, and surgical instrument 4. In FIG. 7, a drive system configuration for one of the surgical instruments 4 is shown, and drive system configurations for the other surgical instruments 4 are omitted.

As shown in FIGS. 1 to 6 and also in FIG. 7, the positioner 7 includes joint drivers D71 to D77 associated with the joints J71 to J77, respectively. The operation of the joint drivers D71 to D77 is controlled by the robot controller 6.

The manipulator 3 includes joint drivers D1 to D8 associated with the joints J1 to J8, respectively. The joint driver D8 for the eighth joint J8 is a slider driver that drives the slider 62. The operation of the joint drivers D1 to D8 is controlled by the robot controller 6. In FIG. 7, a drive system configuration for one of the arms 30 is shown, and drive system configurations for the other arms 30 are omitted.

The surgical instrument 4 includes joint drivers D9 to D12 associated with the joints J9 to J12. The operation of the joint drivers D9 to D12 is controlled by the robot controller 6.

As described above, the positioner 7, manipulator 3, and surgical instrument 4 are provided with joint drivers Dn (n=1 to 12 and 71 to 77). Each joint driver Dn includes a servo motor Mn, a rotation angle sensor En, a reduction gear Rn, and a power transmission mechanism (not shown). The rotation angle sensor En detects the rotation angle of the servo motor Mn and transmits the detected rotation angle to the robot controller 6. The reduction gear Rn reduces the speed output from the servo motor Mn and increases the torque output from the servo motor Mn. The power transmission mechanism transmits the output of the servo motor Mn to the associated link or the like. The power transmission mechanism may be embodied by gears, a transmission wire, a transmission belt, or a combination of the gears, wire, and belt.

[Robot Controller 6]

Figure 8:
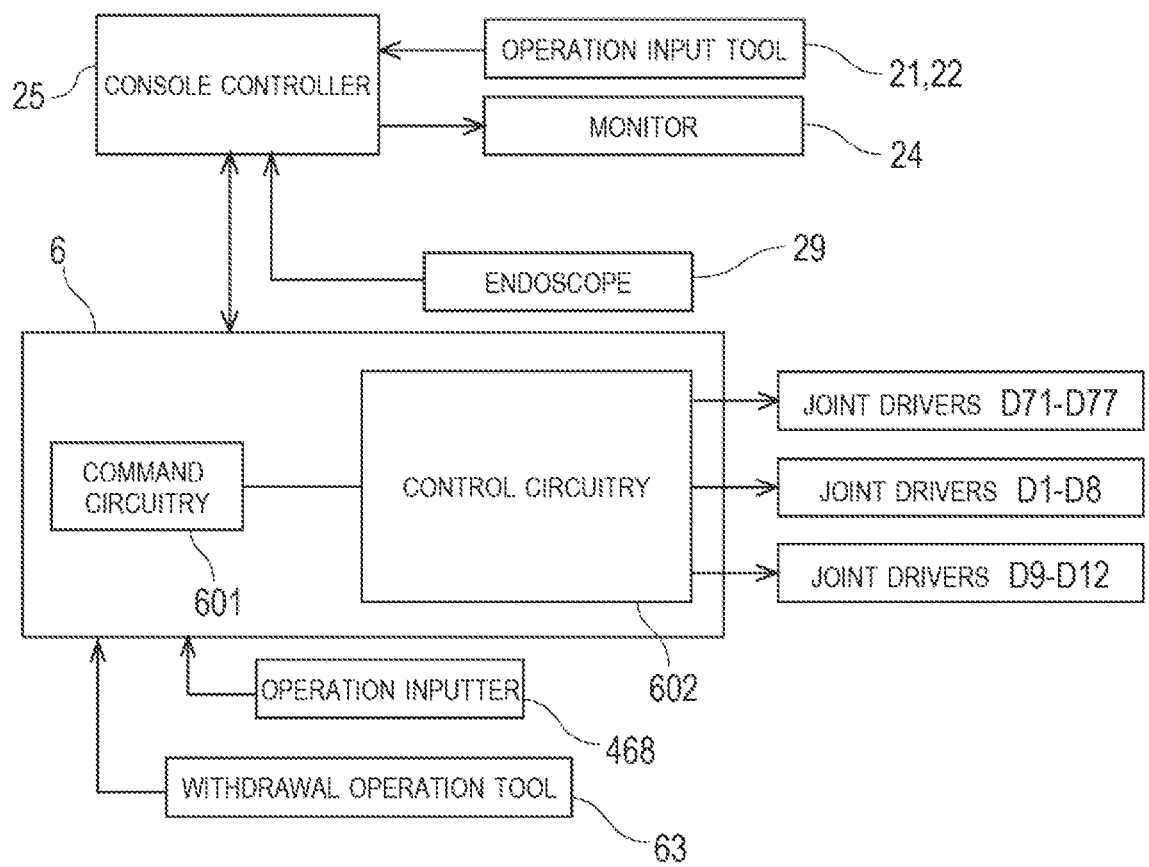
FIG. 8 shows a control system configuration of a surgical system.

The operation of the surgical robot 1A or 1B configured as described above is controlled by the robot controller 6. In the present embodiment, the robot controller 6 is installed inside the cart 9. FIG. 8 shows a control system configuration of the surgical system 100. As shown in FIG. 8, the robot controller 6 includes command circuitry 601 and control circuitry 602. The command circuitry 601 generates operation command signals. The control circuitry 602 receives the command signals and drives the servo motors Mn (n=1 to 12 and 71 to 77) according to the operation commands. The operation commands include position commands.

Figure 9:
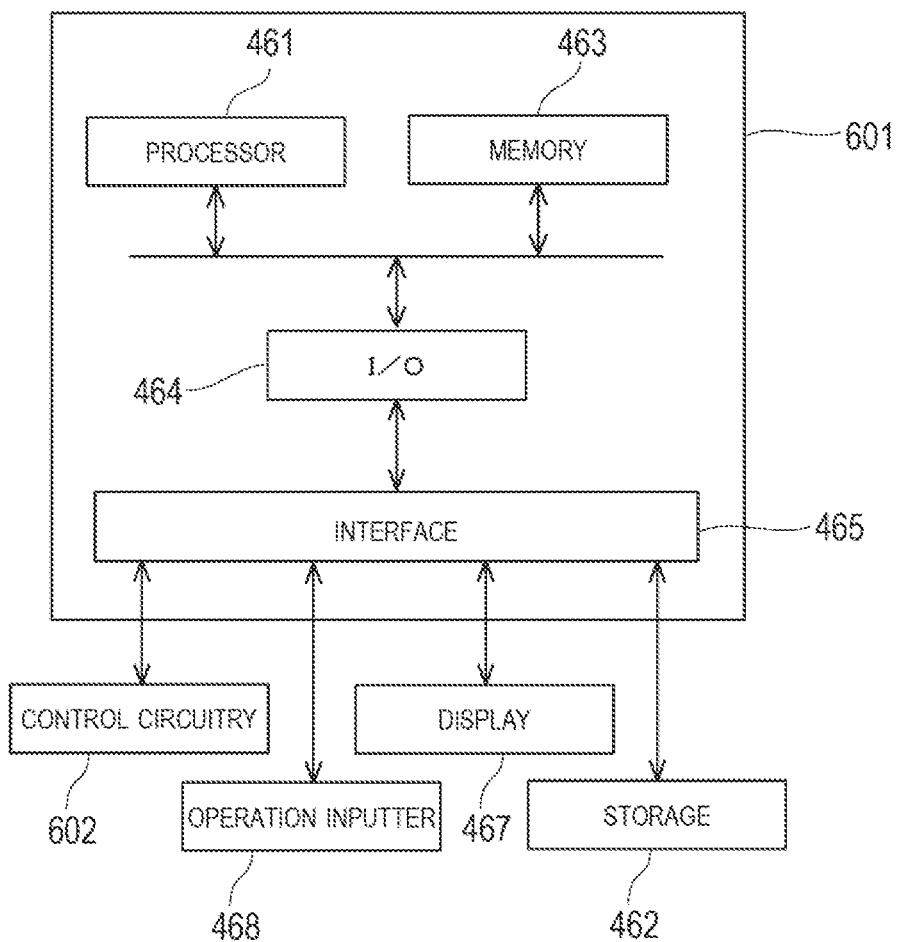
FIG. 9 shows a configuration of command circuitry (processor).

As shown in FIG. 9, the command circuitry 601 includes a processor 461, a memory 463 including a ROM and a RAM, an I/O interface (input/output interface) 464, and communication channels through which the processor 461, memory 463, and I/O interface 464 are connected to one another. A storage 462, a display 467, an operation inputter 468, various sensors, and the control circuitry 602 are connected to the command circuitry 601 via the interface 465.

The command circuitry 601 may include a single processor 461 that performs centralized control or processors 461 that cooperate to perform distributed control. The command circuitry 601 can be configured, for example, by at least one or a combination of two or more of a computer, a personal computer, a microcontroller, a microprocessor, a PLD (programmable logic device) such as an FPGA (field-programmable gate array), a PLC (programmable logic controller), and a logic circuit. Basic programs and software programs executed by the processor 461 are stored in the memory 463 and storage 462. The command circuitry 601 implements the functionality built in a software program through retrieval and execution of the program by the processor 461.

Various pieces of information required for robot-assisted surgery and preparation for the surgery are stored in the memory 463 of the command circuitry 601 or the storage 462. Examples of the pieces of information include information related to the surgical instruments 4, information related to the surgical robot 1A or 1B, information related to the surgical bed 202, information related to the console 2, and information related to the details of the surgery.

As shown in FIG. 7, the control circuitry 602 includes servo amplifiers Cn respectively associated with the servo motors Mn (n=1 to 12 and 71 to 77). The servo amplifiers Cn are electrically connected to the servo motors Mn through amplification circuits or converters which are not shown. Each servo amplifier Cn determines a drive current for the joint Jn as a function of the operation command and supplies the drive current to the servo motor Mn, thereby driving the servo motor Mn.

In the above configuration, the command circuitry 601 acquires operation inputs related to the position and posture of the platform 5 from the operation inputter 468 of the surgical robot 1A or 1B. The command circuitry 601 acquires position information and rotation angle information of each of the joints J71 to J77 based on motor rotation angles detected by the rotation angle sensors E71 to E77, determines those positions and speeds of the joints J71 to J77 of the positioner 7 which are required to place the platform 5 in a target position and posture, and generates position commands matching the acquired operation inputs based on the positions and postures. The generated position commands are transmitted to the control circuitry 602 (servo amplifiers C71 to C77). The control circuitry 602 having acquired the position commands generates drive command values based on the motor rotation angles and position commands and supplies drive currents specified by the drive command values to the servo motors M71 to M77. Thus, the joint drivers D71 to D77 are activated to drive the joints J71 to J77, and the platform 5 is placed in the position and posture matching the operation inputs.

The command circuitry 601 acquires, from the console controller 25, operation inputs related to the position and posture of the surgical instrument 4. The command circuitry 601 acquires position information and rotation angle information of each of the joints J1 to J12 based on motor rotation angles detected by the rotation angle sensors E1 to E12, determines those positions and rotation angles of the joints J1 to J12 which are required to place the tool 48 of the surgical instrument 4 in a target position and posture, and generates position commands matching the acquired operation inputs based on the positions and rotation angles. The generated position commands are transmitted to the control circuitry 602 (servo amplifiers C1 to C12). The control circuitry 602 having acquired the position commands generates drive command values based on the motor rotation angles and position commands and supplies drive currents specified by the drive command values to the servo motors M1 to M12. Thus, the joint drivers D1 to D12 are activated to drive the joints J1 to J12, and the tool 48 of the surgical instrument 4 is placed in the position and posture matching the operations inputs.

[Method of Controlling Surgical Robot 1A or 1B]

When the surgical robot 1A or 1B is in use for surgery, the positioner 7 is basically at rest, the joints J1 to J12 of the manipulator 3 and surgical instrument 4 are driven in response to operation inputs provided to the console 2, and the movement of the joints J1 to J12 results in a change in the position and posture of the tool 48 of the surgical instrument 4.

Before surgery, the cart 9 of the surgical robot 1A or 1B is carried near the surgical bed 202, and the positioner 7 and each manipulator 3 are brought into given preset positions. A teaching tool (not shown) is coupled to the second interface 36 of the manipulator 3. The teaching tool is an imitation of the surgical instrument 4 and, like the surgical instrument 4, includes an interface coupled to the second interface 36. The purpose of the teaching tool is to teach a remote center RC to the surgical robot 1A or 1B. The operator applies an external force to the manipulator 3 equipped with the teaching tool (or the operator maneuvers the manipulator 3 through the operation inputter 468) and thereby moves the teaching tool to a location to be taught to the surgical robot 1A or 1B. The robot controller 6 acquires the position information and rotation angle information of each of the joints J1 to J12 based on motor rotation angles detected by the rotation angle sensors E1 to E12 and uses the acquired pieces of information and other pieces of information such as the property information of the teaching tool to determine the location of the teaching point defined by the teaching tool. The robot controller 6 determines the location of the remote center RC using the location of the teaching point and stores the location of the remote center RC into the memory 463. The remote center RC is the center of the motion of the surgical instrument 4 and is typically set at or near an inlet 200in of a trocar 200 retained at a body wall 204 of the patient 201. The trocar 200 is a tubular device retained at the body wall 204 of the patient 201 to form a surgical port. The trocar 200 includes a sleeve through which the surgical instrument 4 is inserted. Another tubular device such as a cannula, sleeve, or tube may be used instead of the trocar 200. In the above manner, the remote center RC is taught to the robot controller 6 before surgery.

Figure 10:
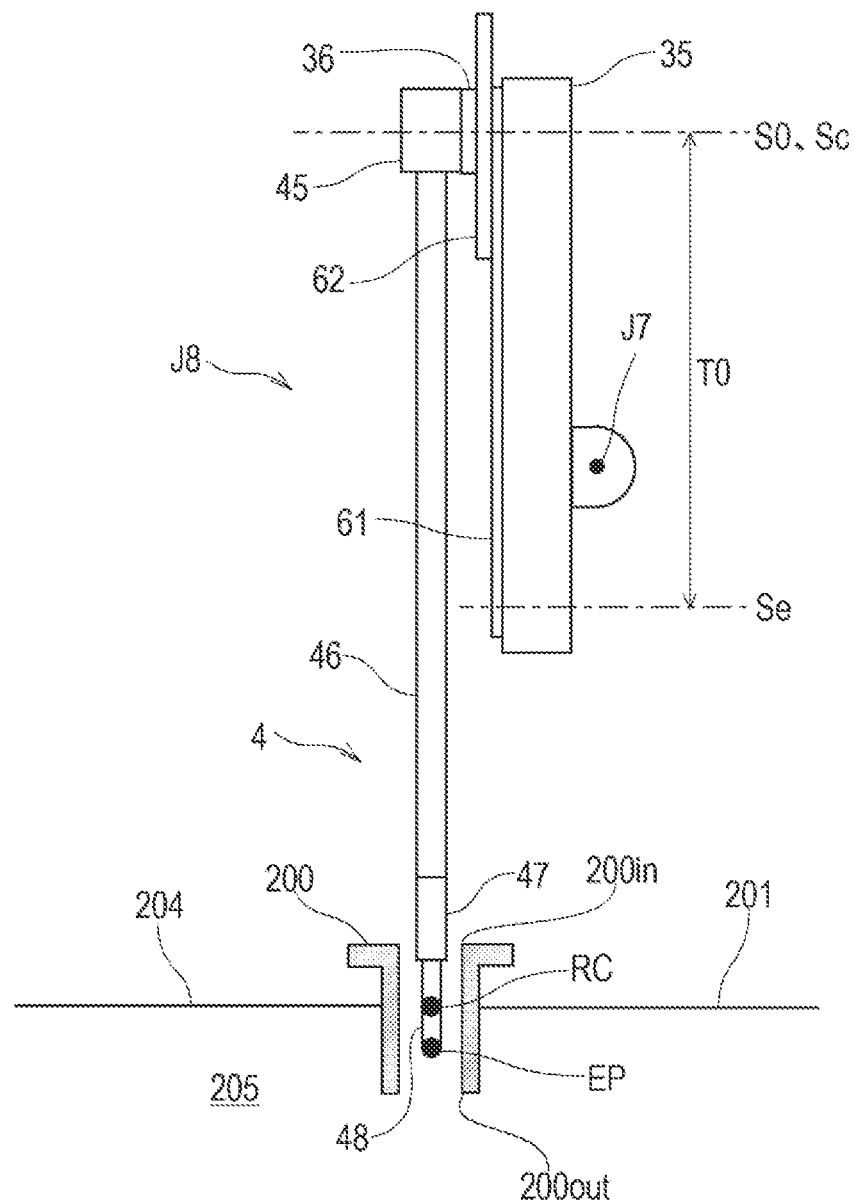
FIG. 10 shows a surgical instrument in a withdrawn position.

FIG. 10 shows the surgical instrument 4 in a withdrawn position to which the surgical instrument 4 has been withdrawn from a body cavity 205. As shown in FIG. 10, when the distal end of the surgical instrument 4 is at a withdrawal point EP, the entirety of the tool 48 is located inside the trocar 200, or a part or the entirety of the tool 48 is located outside the trocar 200 and away from the patient's body, and the tool 48 is not present in the body cavity 205 of the patient 201. The withdrawal point EP is set inside the trocar 200 retained at the body wall 204 of the patient 201. The withdrawal point EP may be set at the inlet 200in or outlet 200out of the trocar 200, but is desirably set between the inlet 200in and outlet 200out. The withdrawal point EP may be set at the same location as the remote center RC. The robot controller 6 may set and store the withdrawal point EP based on the location of the remote center RC.

Figure 11:
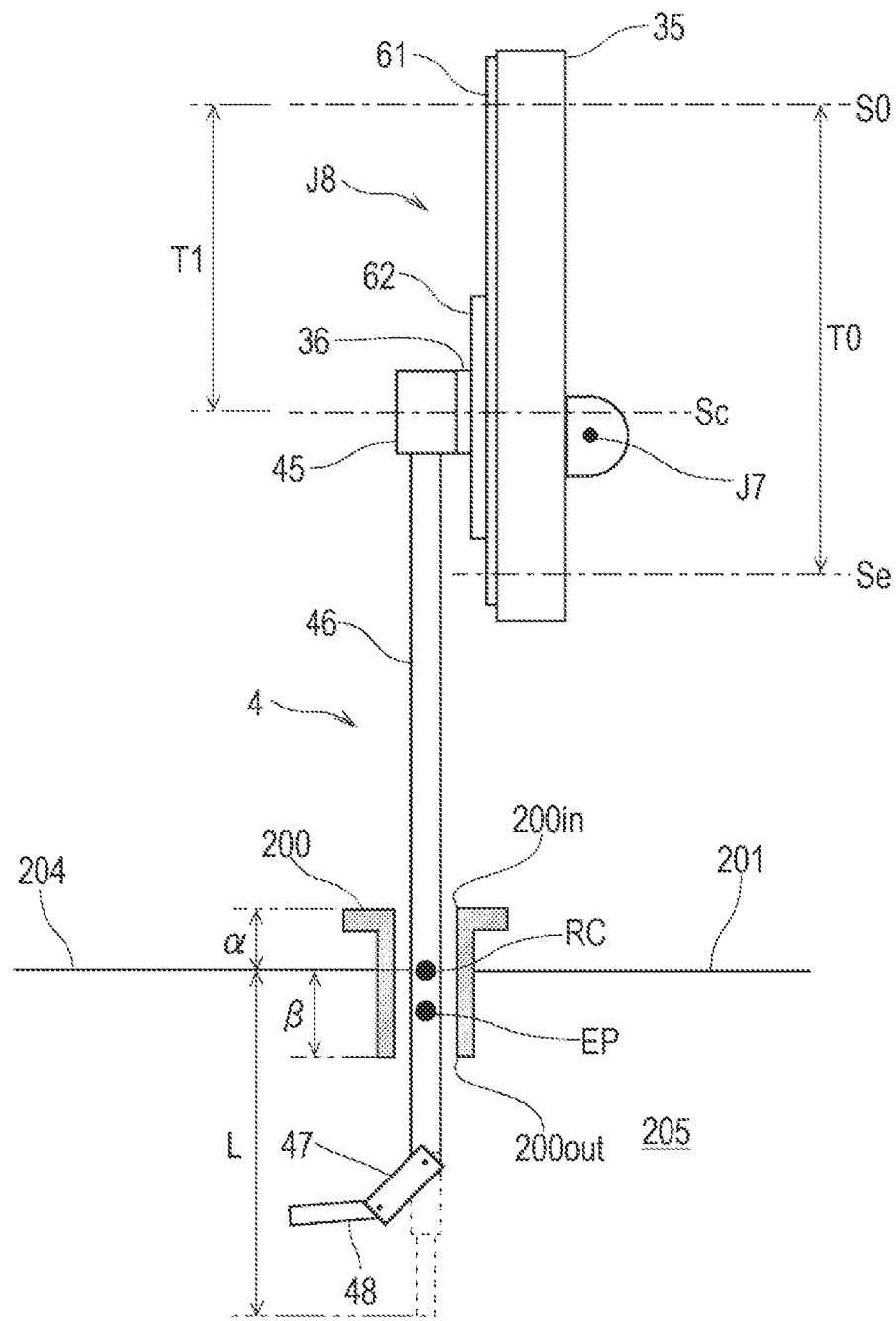
FIG. 11 shows the surgical instrument in an inserted position.

FIG. 11 shows the surgical instrument 4 in an inserted position. In the surgical instrument 4 shown in FIG. 11, the shaft 46 is inserted through the trocar 200, and the tool 48 is located in the body cavity 205 of the patient 201. The distance from the remote center RC to the inlet 200in of the trocar 200 is defined as a distance $\alpha$. The distance $\alpha$ can be a constant in the case where the trocar 200 is placed in the patient in accordance with a non-illustrated reference line of the trocar 200. The distance $\alpha$ varies depending on the type of the trocar 200. The distance from the remote center RC to the outlet 200out of the trocar 200 is defined as a distance $\beta$. The distance $\beta$ can be a constant in the case where the trocar 200 is placed in the patient in accordance with the non-illustrated reference line of the trocar 200.

For the surgical instrument 4 with the tool 48 located in the body cavity 205 of the patient 201, the length from the remote center RC to the distal end of the surgical instrument 4 (i.e., the distal end of the tool 48) is referred to as "intra-body cavity length L" of the surgical instrument 4. The intra-body cavity length L of the surgical instrument 4 is defined based on an operation input that the surgeon 203 provides using the manually-operated manipulator arm 21 of the console 2.

When inserted into or removed out of the body cavity 205 through the trocar 200, the surgical instrument 4 is placed in a posture where the shaft 46, wrist 47, and tool 48 are aligned (this posture will be referred to as "basic posture" hereinafter). The length of the wrist 47 which is included in the intra-body cavity length L is defined as the length of the wrist 47 along the axial direction A0 in the surgical instrument 4 assuming the basic posture. This length is approximately equal to the length of the wrist 47 along its central axis. The length of the tool 48 which is included in the intra-body cavity length L is defined as the length of the tool 48 along the axial direction A0 in the surgical instrument 4 assuming the basic posture. That is, the intra-body cavity length L of the surgical instrument 4 is calculated on the supposition that the surgical instrument 4 is in the basic posture, regardless of the actual postures of the wrist 47 and tool 48.

In the present embodiment, the intra-body cavity length L of the surgical instrument 4 can be determined based on the position and posture of the second interface 36, the location of the remote center RC, and dimensional information of the surgical instrument 4. The dimensional information of the surgical instrument 4 includes, for example, the size of the base 45, the length of the shaft 46, the link length of the wrist 47, and the length of the jaw members 481 of the tool 48. The position and posture of the second interface 36 can be determined based on the rotation angles detected by the rotation angle sensors E1 to E8 and dimensional information of the manipulator 3. The way of calculating the intra-body cavity length L of the surgical instrument 4 is not limited to that described above.

An origin position S0 and an end point position Se are predefined for the eighth joint J8 of the manipulator 3 The origin position S0 is defined at or near the proximal end of the rail 61. The end point position Se is defined at or near the distal end of the rail 61. The current sliding position of the slider 62 is referred to as "current position Sc". The amount of linear movement of the eighth joint J8 from the origin position S0 to the end point position Se along the axial direction A0 is referred to as "maximum possible linear movement amount T0" of the eighth joint J8. The amount of linear movement of the eighth joint J8 from the origin position S0 to the current position Sc along the axial direction A0 is referred to as "first linear movement amount T1" of the eighth joint J8.

During surgery, the first linear movement amount T1 of the eighth joint J8 is kept equal to or in a given relationship with the intra-body cavity length L of the surgical instrument 4 in the case where the intra-body cavity length L of the surgical instrument 4 is equal to or smaller than the maximum possible linear movement amount T0. The robot controller 6 controls the motion of the manipulator 3 such that the relationship T1=L is established between the intra-body cavity length L of the surgical instrument 4 and the first linear movement amount T1 of the eighth joint J8. Specifically, the robot controller 6 drives the eighth joint J8 such that the intra-body cavity length L and the first linear movement amount T1 are equal. At the same time, the robot controller 6 drives the joints of the manipulator 3 other than the eighth joint J8, i.e., the joints J1 to J7, and the joints J9 to J12 of the surgical instrument 4 such that the tool 48 is placed in a position and posture matching the command. That is, in the case where a command to move the distal end of the surgical instrument 4 in the axial direction A0 is given through the manually-operated manipulator arm 21 and where the distal end of the surgical instrument 4 can be moved to the commanded position only by linear movement of the eighth joint J8, the robot controller 6 moves the surgical instrument 4 in the axial direction A0 by using only the eighth joint J8 of the manipulator 3 without using the rotational joints J1 to J7 of the manipulator 3.

The robot controller 6 performs withdrawal control to withdraw the surgical instrument 4 from the body cavity 205 of the patient 201 in response to a withdrawal signal provided as a trigger. The withdrawal signal can be generated by operating a withdrawal operation tool 63 of the manipulator 3. Each of the manipulators 3 of the surgical robot 1A or 1B is equipped with the withdrawal operation tool 63 (see FIGS. 2 and 8). The withdrawal operation tool 63 may be, for example, a simple operation tool such as a button, lever, or pedal.

Once the withdrawal operation tool 63 is operated during surgery, the withdrawal signal is provided to the robot controller 6. The robot controller 6 performs the withdrawal control immediately upon receiving the withdrawal signal. Specifically, the robot controller 6 drives the eighth joint J8 of the manipulator 3 to move (return) the slider 62 from the current position Sc to the origin position S0 while keeping the positions and rotation angles of the joints J1 to J7 of the manipulator 3 unchanged. At the same time, the robot controller 6 drives the wrist joints J9 to J11 and tool joint J12 of the surgical instrument 4 as necessary to place the surgical instrument 4 in the basic posture.

As shown in FIG. 10, the withdrawal control allows the shaft 46 of the surgical instrument 4 to be pulled out of the trocar 200 along the axial direction A0 and the distal end of the surgical instrument 4 to reach the withdrawal point EP. As a result, the tool 48 of the surgical instrument 4 is withdrawn from the body cavity 205 of the patient 201.

As described above, a surgical robot 1A or 1B of the present embodiment includes: a surgical instrument 4; a manipulator 3 that supports the surgical instrument 4 without holding a trocar 200 retained at a body wall 204 of a patient 201; and a robot controller 6. The surgical instrument 4 includes: a base 45 disposed at a proximal end of the surgical instrument 4; a tool 48 disposed at a distal end of the surgical instrument 4; and a shaft 46 extending in an axial direction A0 between the base 45 and the tool 48. The manipulator 3 includes: an instrument interface 36 to which the base 45 is attached; an arm 30 including rotational joints (first to seventh joints J1 to J7); and a prismatic joint (eighth joint J8) coupling the instrument interface 36 to the arm 30.

In the surgical robot 1A or 1B configured as described above, the robot controller 6 stores a remote center RC. Additionally, the robot controller 6 controls motion of the manipulator 3 such that with the shaft 46 inserted through the trocar 200 and the tool 48 located in a body cavity 205 of the patient 201, a relationship T1=L is established between an intra-body cavity length L of the surgical instrument 4 and a first linear movement amount T1 of the prismatic joint (eighth joint J8). The intra-body cavity length L of the surgical instrument 4 represents the length from the remote center RC to the distal end of the surgical instrument 4. The first linear movement amount T1 of the prismatic joint (eighth joint J8) represents the amount of linear movement of the prismatic joint (eighth joint J8) from an origin position S0 to a current position Sc along the axial direction A0. A maximum possible linear movement amount T0 of the prismatic joint (eighth joint J8) represents the amount of linear movement of the prismatic joint (eighth joint J8) from the origin position S0 to an end point position Se along the axial direction A0.

A method of controlling the surgical robot 1A or 1B according to the present embodiment includes:
storing a remote center RC that is a center of motion of the surgical instrument 4; and
controlling motion of the manipulator 3 such that with the shaft 46 inserted through the trocar 200 and the tool 48 located in the body cavity 205 of the patient 201, a relationship T1=L is established between the intra-body cavity length L of the surgical instrument 4 and the first linear movement amount T1 of the prismatic joint (eighth joint J8).

Although in the above embodiment the distal end of the tool 48 of the surgical instrument 4 is moved to the withdrawal point EP in the withdrawal control, the distal end of the tool 48 may be moved beyond the withdrawal point EP towards the outside of the patient's body. From this viewpoint, the robot controller 6 may control the motion of the manipulator 3 such that with the shaft 46 inserted through the trocar 200 and the tool 48 located in the body cavity 205 of the patient 201, a relationship T1≥L is established between the intra-body cavity length L of the surgical instrument 4 and the first linear movement amount T1 of the prismatic joint (eighth joint J8).

Likewise, the method of controlling the surgical robot 1A or 1B may include:

storing a remote center RC that is a center of motion of the surgical instrument 4; and controlling motion of the manipulator 3 such that with the shaft 46 inserted through the trocar 200 and the tool 48 located in the body cavity 205 of the patient 201, a relationship T1≥L is established between the intra-body cavity length L of the surgical instrument 4 and the first linear movement amount T1 of the prismatic joint (eighth joint J8).

In the surgical robot 1A or 1B and control method thereof, moving the distal end of the tool 48 out of the patient's body and much away from the inlet 200in of the trocar 200 could cause scattering of the body fluid carried on the tool 48 or complicate the next insertion of the tool 48 into the trocar 200. From this viewpoint, the robot controller 6 may control the motion of the manipulator 3 such that with the shaft 46 inserted through the trocar 200 and the tool 48 located in the body cavity 205 of the patient 201, a relationship (L−β)≤T1≤(L+α) is established among the intra-body cavity length L of the surgical instrument 4, the first linear movement amount T1 of the prismatic joint (eighth joint J8), a distance α from the remote center RC to the inlet 200in of the trocar 200, and a distance β from the remote center RC to the outlet 200out of the trocar 200.

Likewise, the method of controlling the surgical robot 1A or 1B may include:

storing a remote center RC that is a center of motion of the surgical instrument 4; and controlling motion of the manipulator 3 such that with the shaft 46 inserted through the trocar 200 and the tool 48 located in the body cavity 205 of the patient 201, a relationship (L−β)≤T1≤(L+α) is established among the intra-body cavity length L of the surgical instrument 4, the first linear movement amount T1 of the prismatic joint (eighth joint J8), a distance a from the remote center RC to the inlet 200in of the trocar 200, and a distance β from the remote center RC to the outlet 200out of the trocar 200.

In the above configuration, the first linear movement amount T1 may vary in the range of (L−β) to (L+α) or may be controlled to a given value in the range of (L−β) to (L+α).

In the surgical robot 1A or 1B and control method thereof, the tool 48 of the surgical instrument 4 can be withdrawn from the body cavity 205 of the patient 201 into the trocar 200 only by the control (withdrawal control) for returning the prismatic joint (eighth joint J8) of the manipulator 3 to the origin position S0 since the maximum possible linear movement amount T0 of the prismatic joint (eighth joint J8) of the manipulator 3 is equal to or greater than the intra-body cavity length L of the surgical instrument 4.

In the withdrawal control, the shaft 46 of the surgical instrument 4 moves only along the axial direction A0. This reduces shaking of the shaft 46, making galling less likely to occur between the trocar 200 and the shaft 46. Since the shaft 46 can be smoothly pulled out of the trocar 200, the load imposed on the body wall 204 of the patient 201 can be reduced.

In the withdrawal control, the motion of the joints of the positioner 7 and manipulator 3 other than the eighth joint J8 of the manipulator 3, i.e., the motion of all of the joints J71 to J77 and J1 to J7, is constrained, and only the joint driver D8 for the eighth joint J8 of the manipulator 3 is operated. It is also possible to pull the surgical instrument 4 out of the body cavity 205 by driving the joints J1 to J8 of the manipulator 3 instead of driving the eighth joint J8 alone. However, with the use of the above withdrawal control, in which the joint to be driven is limited to the eighth joint J8 and in which the target position of the eighth joint J8 is the origin position S0 regardless of the current position Sc, processing procedures performed by the robot controller 6 are simplified, and quick withdrawal can be expected.

Furthermore, in the surgical robot 1A or 1B configured as described above and the control method thereof, the manipulator 3 supporting the surgical instrument 4 is independent of the trocar 200. Thus, the manipulator 3 can move without being constrained by the trocar 200. This allows for increased flexibility in the design of the manipulator 3. Additionally, there is no need to remove the trocar 200 from the manipulator 3 when withdrawing the manipulator 3 from the patient, and the withdrawal of the manipulator 3 from the patient can be quickly accomplished.

Furthermore, in the surgical robot 1A or 1B configured as described above and the control method thereof, the trocar 200 is not held by any instrument holder supporting the surgical instrument 4, unlike in conventional surgical robots. This can reduce the crowding of instrument holders around the surgical site. Even in the case where the surgical instrument 4 is inserted as deeply as possible, the prismatic joint (eighth joint J8) and the manipulator 3 do not interfere with the patient 201, and the distance from the prismatic joint (eighth joint J8) and manipulator 3 to the patient 201 can be kept large enough to prevent interference of the prismatic joint (eighth joint J8) and manipulator 3 with the patient 201.

In the surgical robot 1A or 1B according to the present embodiment, the robot controller 6 is configured to, in response to a withdrawal signal provided as a trigger, move the prismatic joint (eighth joint J8) to the origin position S0 while constraining motion of the rotational joints J1 to J7 of the arm 30 of the manipulator 3.

Likewise, the method of controlling the surgical robot 1A or 1B according to the present embodiment includes, in response to a withdrawal signal provided as a trigger, moving the prismatic joint (eighth joint J8) to the origin position S0 while constraining motion of the rotational joints J1 to J7 of the arm 30 of the manipulator 3.

In the surgical robot 1A or 1B and control method thereof, providing the withdrawal signal to the robot controller 6 can cause the robot controller 6 to perform the withdrawal control. In the surgical robot 1A or 1B configured as described above, the withdrawal of the surgical instrument 4 from the body cavity 205 of the patient 201 can be accomplished quickly and reliably as previously stated. Such withdrawal control is beneficial not only for inserting or removing the surgical instrument 4 into or out of the body cavity 205 of the patient 201 but also for withdrawing the surgical instrument 4 from the body cavity 205 in the event of an emergency situation.

Although the foregoing has described a preferred embodiment of the present invention, the scope of the present invention embraces modifications made to the details of the structure and/or function of the above embodiment without departing from the gist of the present invention.

For example, while the tool 48 of the surgical instrument 4 is in the form of forceps in the above embodiment, the tool 48 is not limited to this form. The tool 48 may be any tool selected from the group consisting of tools having movable joints and tools having no joints. Examples of the tools having movable joints include forceps, scissors, graspers, needle holders, microdissectors, staple appliers, tackers, suction and irrigation tools, snare wires, and clip appliers. Examples of the tools having no joints include cutting blades, cautery probes, irrigators, catheters, and suction orifices.

For example, while in the above embodiment the manipulator 3 has eight joints (controlled axes) including the eighth joint J8 which is a prismatic joint, the number of the joints of the manipulator 3 is not limited to eight.

For example, in the above embodiment, the eighth joint J8 is constructed of a single-stage linear-motion mechanism. The eighth joint J8 may be constructed of a multi-stage linear-motion mechanism, and the motion of the eighth joint J8 may be controlled such that the sum of the movement amounts of all the stages is the first linear movement amount T1.

In the above embodiment, motion control performed by the robot controller 6 on the eighth joint J8 which is a prismatic joint has been described for the case where the intra-body cavity length L of the surgical instrument 4 is equal to or smaller than the maximum possible linear movement amount T0 (L≤T0). Driving only one joint as in the above motion control is advantageous in that shaking of the shaft 46 passing through the trocar 200 can be reduced and the passing speed of the shaft 46 can be increased. The following describes motion control performed by the robot controller 6 on the manipulator 3 in the case where the intra-body cavity length L of the surgical instrument 4 is greater than the maximum possible linear movement amount T0 (L>T0).

Figure 12:
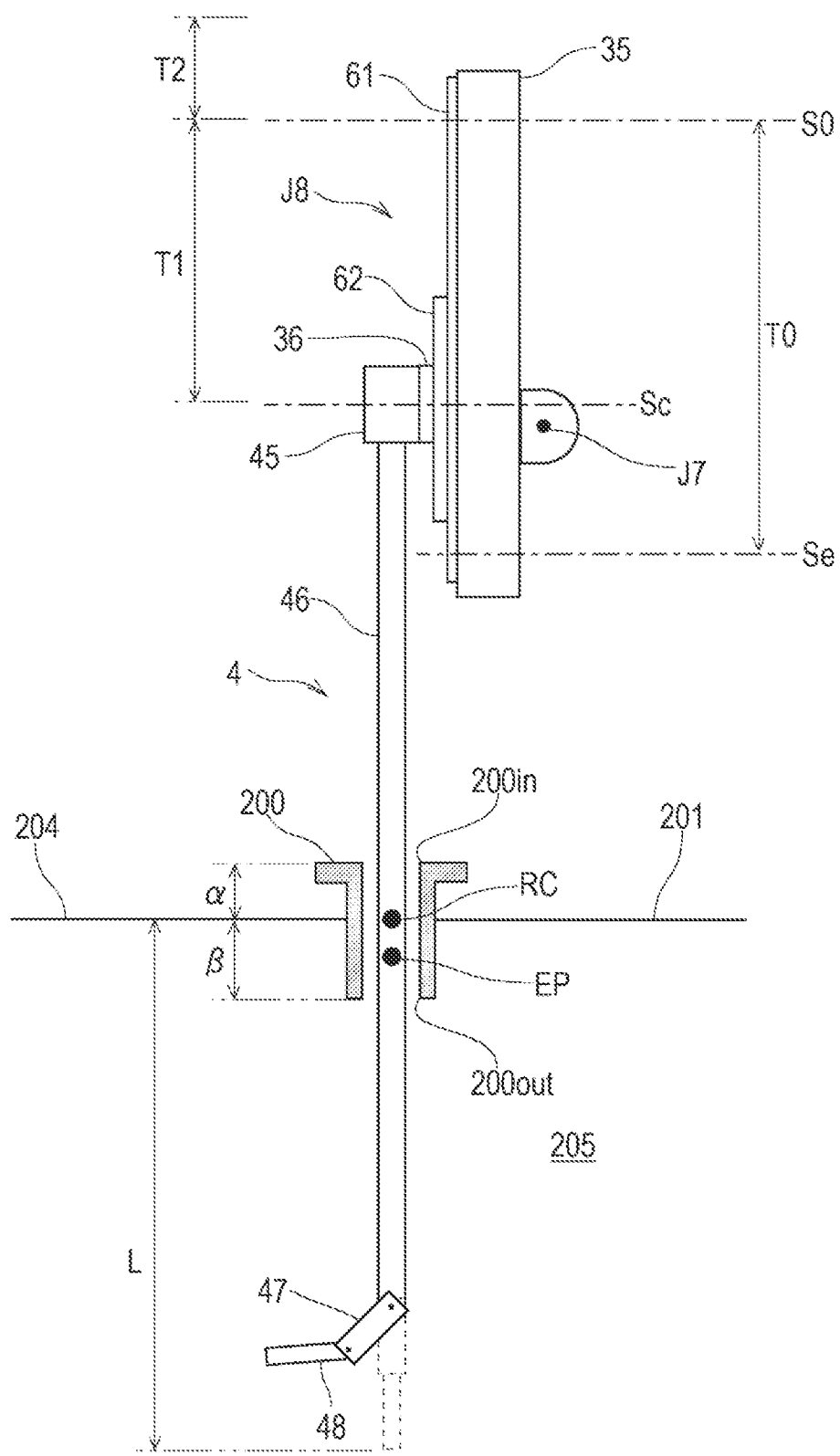
FIG. 12 shows another situation for the surgical instrument in an inserted position.

As shown in FIG. 12, the amount by which the distal end of the surgical instrument 4 can be linearly moved along the axial direction A0 by at least one of the joints of the manipulator 3 other than the eighth joint J8, namely at least one of the rotational joints J1 to J7, is referred to as "second linear movement amount T2". It should be noted that the second linear movement amount T2 is not limited to an amount of strictly linear motion. Each of the rotational joints J1 to J7 rotates about a rotation center. In the case where the amount of rotation is small, a portion of the surgical instrument 4 that passes through the remote center RC can move substantially linearly. The movement with the second linear movement amount T2 is preferably effected by six joints of the manipulator 3 other than the eighth joint J8, namely by six of the rotational joints J1 to J7, in order to enhance the linearity of the movement.

The second linear movement amount T2 may be variable depending on the difference between the intra-body cavity length L of the surgical instrument 4 and the maximum possible linear movement amount T0. The second linear movement amount T2 is preferably smaller than the first linear movement amount T1 in order to accomplish quick withdrawal motion in the withdrawal process.

As described above, the robot controller 6 may control the motion of the manipulator such that with the shaft 46 inserted through the trocar 200 and the tool 48 located in the body cavity 205 of the patient 201, a relationship (T1+T2) ≥L is established, wherein: L represents an intra-body cavity length of the surgical instrument 4, the intra-body cavity length being a length from the remote center RC to the distal end of the surgical instrument 4; T1 represents a first linear movement amount of the prismatic joint J8 of the manipulator 3, the first linear movement amount being an amount of linear movement from an origin position to a current position along the axial direction A0; and T2 represents a second linear movement amount of the distal end of the arm 30, the second linear movement amount being an amount of linear movement effected along the axial direction A0 by at least one of the rotational joints J1 to J7 of the manipulator 3. That is, in the case where a command to move the distal end of the surgical instrument 4 in the axial direction A0 is given through the manually-operated manipulator arm 21 but the linear movement of the eighth joint J8 alone is insufficient to move the distal end of the surgical instrument 4 to the commanded position, the robot controller 6 can move the surgical instrument 4 in the axial direction A0 by using the eighth joint J8 and at least one of the rotational joints J1 to J7 of the manipulator 3.

Once the withdrawal operation tool 63 is operated during the above control of the manipulator 3, a withdrawal signal is provided to the robot controller 6. The robot controller 6 carries out withdrawal control immediately upon receiving the withdrawal signal. Specifically, in order to move the distal end of the surgical instrument 4 to the withdrawal point EP, the robot controller 6 drives the eighth joint J8 to move (return) the slider 62 from the current position Sc to the origin position S0 and further drives two or more of the joints J1 to J7 of the manipulator 3. At the same time, the robot controller 6 drives the wrist joints J9 to J11 and tool joint J12 of the surgical instrument 4 as necessary to place the surgical instrument 4 in the basic posture. The withdrawal control allows the shaft 46 of the surgical instrument 4 to be pulled out of the trocar 200 along the axial direction A0 and the distal end of the surgical instrument 4 to reach the withdrawal point EP.

In the withdrawal process, in the case where the intra-body cavity length L is smaller than the maximum possible linear movement amount T0, the manipulator 3 is desirably controlled such that only the eighth joint J8 is preferentially driven while the rotational joints J1 to J7 remain at rest. In the case where the intra-body cavity length L is greater than the maximum possible linear movement amount T0 (L>T0), the first linear movement amount T1 is preferably equal to the maximum possible linear movement amount T0, and the robot controller 6 may control the motion of the manipulator 3 such that a relationship T2≥(L−T0) is established.

In the withdrawal process, in the case where at least one of the rotational joints J1 to J7 is permitted to be driven in addition to the prismatic joint J8, the robot controller 6 may move the eighth joint J8, which is a prismatic joint, to the origin position and drive two or more of the rotational joints J1 to J7 to move the distal end of the arm 30 away from the trocar 200 along the axial direction A0 by an amount corresponding to the difference between the intra-body cavity length L and the maximum possible linear movement amount T0. In this case, six of the rotational joints J1 to J7 are preferably driven to enhance the linearity of the withdrawal movement. Driving the prismatic joint J8 preferentially over the rotational joints J1 to J7 makes it possible to pull out the surgical instrument 4 quickly.

The invention claimed is:
1. A surgical robot comprising:
a surgical instrument including a base disposed at a proximal end of the surgical instrument, a tool disposed at a distal end of the surgical instrument, and a shaft extending in an axial direction between the base and the tool;

a manipulator configured to support the surgical instrument without holding a trocar retained at a body wall of a patient, the manipulator including an instrument interface to which the base of the surgical instrument is attached, an arm including rotational joints, and a prismatic joint coupling the instrument interface to a distal end of the arm; and a controller including a memory that stores a remote center that is a center of motion of the surgical instrument, wherein the controller is configured to control a motion of the manipulator such that a relationship $(L-\beta) \leq T1 \leq (L+\alpha)$ is established in a case of $L \leq T0$, L represents an intra-body cavity length of the surgical instrument, the intra-body cavity length being a length from the remote center to the distal end of the surgical instrument; T0 represents a maximum possible linear movement amount of the prismatic joint, the maximum possible linear movement amount being an amount of movement from an origin position to an end point position; and T1 represents a first linear movement amount of the prismatic joint, the first linear movement amount being an amount of movement from the origin position to a current position, and the controller is configured to control the motion of the manipulator such that the relationship $(L-\beta) \leq T1 \leq (L+\alpha)$ is established among the intra-body cavity length L, the first linear movement amount T1, a distance $\alpha$ from the remote center to an inlet of the trocar, and a distance $\beta$ from the remote center to an outlet of the trocar.

2. The surgical robot according to claim 1, wherein the controller is configured to control the motion of the manipulator such that a relationship T1=L is established between the intra-body cavity length L and the first linear movement amount T1.

3. The surgical robot according to claim 1, wherein the controller is configured to, in response to a withdrawal signal provided as a trigger, move the prismatic joint to the origin position while constraining motion of the rotational joints of the arm.

4. The surgical robot according to claim 1, wherein the controller is configured to control the motion of the manipulator such that a relationship $(T1+T2) \geq L$ is established in case of $L>T0$, wherein T2 represents a second linear movement amount of the distal end of the arm, the second linear movement amount being an amount of movement effected along the axial direction of the shaft by motion of at least one of the rotational joints of the arm.

5. The surgical robot according to claim 4, wherein the second linear movement amount T2 is smaller than the first linear movement amount T1.

6. The surgical robot according to claim 4, wherein the controller is configured to, in response to a withdrawal signal provided as a trigger, move the prismatic joint to the origin position and drive the at least one rotational joint to move the distal end of the arm away from the trocar along the axial direction by an amount corresponding to a difference between the intra-body cavity length L and the first linear movement amount T1.

7. The surgical robot according to claim 4, wherein the controller is configured to control the motion of the manipulator such that a relationship $(T0+T2) \geq L$ is established in case of $L>T0$.

8. A method of controlling a surgical robot, the surgical robot including: a surgical instrument including a base disposed at a proximal end of the surgical instrument, a tool disposed at a distal end of the surgical instrument, and a shaft extending in an axial direction between the base and the tool; and a manipulator configured to support the surgical instrument without holding a trocar retained at a body wall of a patient, the manipulator including an instrument interface to which the base of the surgical instrument is attached, an arm including rotational joints, and a prismatic joint coupling the instrument interface to a distal end of the arm, the method comprising:

storing a remote center that is a center of motion of the surgical instrument;

receiving an operation for moving the surgical instrument; and controlling motion of the manipulator such that with the shaft inserted through the trocar and the tool located in a body cavity of the patient, a relationship $(L-\beta) \leq T1 \leq (L+\alpha)$ is established in case of $L \leq T0$, wherein: L represents an intra-body cavity length of the surgical instrument, the intra-body cavity length being a length from the remote center to the distal end of the surgical instrument; T0 represents a maximum possible linear movement amount of the prismatic joint, the maximum possible linear movement amount being an amount of movement from an origin position to an end point position; and T1 represents a first linear movement amount of the prismatic joint, the first linear movement amount being an amount of movement from the origin position to a current position, wherein controlling the motion of the manipulator comprises controlling the motion of the manipulator such that the relationship $(L-\beta) \leq T1 \leq (L+\alpha)$ is established among the intra-body cavity length L, the first linear movement amount T1, a distance $\alpha$ from the remote center to an inlet of the trocar, and a distance $\beta$ from the remote center to an outlet of the trocar.

9. The method according to claim 8, wherein in the controlling the motion of the manipulator, the motion of the manipulator is controlled such that a relationship T1=L is established between the intra-body cavity length L and the first linear movement amount T1.

10. The method according to claim 8, further comprising, in response to a withdrawal signal provided as a trigger, moving the prismatic joint to the origin position while constraining motion of the rotational joints of the arm.

11. The method according to claim 8, wherein in the controlling the motion of the manipulator, the motion of the manipulator is controlled such that a relationship $(T1+T2) \geq L$ is established in case of $L>T0$, wherein T2 represents a second linear movement amount of the distal end of the arm, the second linear movement amount being an amount of movement effected along the axial direction of the shaft by motion of at least one of the rotational joints of the arm.

12. The method according to claim 11, wherein the second linear movement amount T2 is smaller than the first linear movement amount T1.

13. The method according to claim 11, further comprising, in response to a withdrawal signal provided as a trigger, moving the prismatic joint to the origin position and driving the at least one rotational joint to move the distal end of the arm away from the trocar along the axial direction by an amount corresponding to a difference between the intra-body cavity length L and the first linear movement amount T1.

14. The method according to claim 11, wherein in the controlling the motion of the manipulator, the motion of the manipulator is controlled such that a relationship (T0+T2) ≥L is established in case of L>T0.

15. A surgical system comprising:
a surgical instrument including a base disposed at a proximal end of the surgical instrument, a tool disposed at a distal end of the surgical instrument, and a shaft extending in an axial direction between the base and the tool;
a manipulator configured to support the surgical instrument without holding a trocar retained at a body wall of a patient, the manipulator including an instrument interface to which the base of the surgical instrument is attached, an arm including rotational joints, and a prismatic joint coupling the instrument interface to a distal end of the arm;
an operation input tool that receives an operation for moving the surgical instrument; and
a controller including a memory that stores a remote center that is a center of motion of the surgical instrument and configured to control the manipulator such that the surgical instrument moves based on the operation received by the operation input tool, wherein
the controller is further configured to, based on the operation received by the operation input tool,
control motion of the manipulator such that a relationship (L−β)≤T1≤(L+α) is established in a case of L≤T0, wherein: L represents an intra-body cavity length of the surgical instrument, the intra-body cavity length being a length from the remote center to the distal end of the surgical instrument; T0 represents a maximum possible linear movement amount of the prismatic joint, the maximum possible linear movement amount being an amount of movement from an origin position to an end point position; and T1 represents a first linear movement amount of the prismatic joint, the first linear movement amount being an amount of movement from the origin position to a current position, and
the controller is configured to control the motion of the manipulator such that the relationship (L−β)≤T1≤(L+α) is established among the intra-body cavity length L, the first linear movement amount T1, a distance α from the remote center to an inlet of the trocar, and a distance β from the remote center to an outlet of the trocar.

16. The surgical system according to claim 15, wherein the controller is configured to control the motion of the manipulator such that a relationship (T1+T2)≥L is established in case of L>T0, wherein T2 represents a second linear movement amount of the distal end of the arm, the second linear movement amount being an amount of movement effected along the axial direction of the shaft by motion of at least one of the rotational joints of the arm.

17. The surgical system according to claim 16, wherein the second linear movement amount T2 is smaller than the first linear movement amount T1.

18. The surgical system according to claim 16, wherein the controller is configured to control the motion of the manipulator such that a relationship (T0+T2)≥L is established in case of L>T0.

* * * * *

UNITED STATES PATENT AND TRADEMARK OFFICE
CERTIFICATE OF CORRECTION

| | |
|---|---|
| PATENT NO. | : 12,245,832 B2 |
| APPLICATION NO. | : 17/782216 |
| DATED | : March 11, 2025 |
| INVENTOR(S) | : Tsuyoshi Tojo et al. |

It is certified that error appears in the above-identified patent and that said Letters Patent is hereby corrected as shown below:

On the Title Page

Item (71) should read:
KAWASAKI JUKOGYO KABUSHIKI KAISHA, Kobe (JP)

Signed and Sealed this
Twenty-second Day of April, 2025

Coke Morgan Stewart
*Acting Director of the United States Patent and Trademark Office*